United States Patent [19]

Rytter et al.

[11] Patent Number: 5,407,644
[45] Date of Patent: Apr. 18, 1995

[54] CATALYTIC MULTI-PHASE REACTOR

[75] Inventors: Erling Rytter; Petter Lian; Trond Myrstad, all of Trondheim; Per T. Roterud, Stathelle; Age Solbakken, Trondheim, all of Norway

[73] Assignee: Den Norske Stats Oljesselskap A.S., Stavanger, Norway

[21] Appl. No.: 21,898

[22] Filed: Feb. 24, 1995

[30] Foreign Application Priority Data

Feb. 25, 1992 [GB] United Kingdom ............... 9203958

[51] Int. Cl.⁶ ............................ B01J 8/22; B01F 3/04; B01F 3/12
[52] U.S. Cl. .................................. 422/147; 422/140; 422/231
[58] Field of Search ............... 422/106, 108, 231, 110, 422/111, 145, 147, 213, 218, 140, 143; 210/289, 291

[56] References Cited

U.S. PATENT DOCUMENTS

| | | | |
|---|---|---|---|
| 2,668,622 | 2/1954 | Irvine et al. | 210/289 X |
| 3,027,244 | 3/1962 | Byrne et al. | 422/218 |
| 3,167,399 | 5/1962 | Hansen | 422/218 X |
| 3,235,343 | 2/1966 | Riggens | 422/218 X |
| 3,844,936 | 10/1974 | Newson | 422/218 X |
| 3,909,208 | 9/1975 | Boret et al. | 422/218 |
| 4,033,727 | 7/1977 | Vautrain | 422/218 |
| 4,107,553 | 9/1979 | Persico et al. | 422/218 X |
| 4,374,095 | 2/1983 | Legg et al. | 422/218 |
| 4,446,112 | 5/1984 | Den Hartog | 422/220 X |
| 4,464,255 | 8/1984 | Ueda | 210/289 X |
| 4,579,647 | 4/1986 | Smith | 422/220 X |
| 4,714,592 | 12/1987 | Zanma et al. | 422/218 X |
| 4,859,427 | 8/1989 | Konishi et al. | 422/171 X |
| 4,937,051 | 6/1990 | Graven et al. | 422/106 X |
| 4,952,302 | 8/1990 | Leach | 422/106 X |
| 5,061,450 | 10/1991 | Aoyagi | 422/106 X |
| 5,160,428 | 11/1992 | Kuri | 210/108 X |
| 5,174,877 | 12/1992 | Cooper et al. | 204/193 |

Primary Examiner—Robert J. Warden
Assistant Examiner—Robert Carpenter
Attorney, Agent, or Firm—Kirkpatrick & Lockhart

[57] ABSTRACT

A reactor for conducting a continuous multi-phase catalytic reaction such as the conversion of syngas to higher hydrocarbon fuels. Gaseous reactants are introduced via a gas-permeable plate into a slurry which includes the product and a finely divided catalyst. The liquid product is separated from the remainder of the slurry by means of a filter unit including a filter member. A pressure differential is established across the filter member by means of a constant level device within the filter unit which maintains a level of filtrate within the filter unit below the level of the slurry. The slurry is maintained in a constant state of agitation by the introduction of the gaseous components as a steam of bubbles. Fluctuations in the pressure differential across the filter member prevent the filter member from clogging and the gas spaces above the filtrate and the slurry are in communication.

27 Claims, 3 Drawing Sheets

CATALYTIC MULTI-PHASE REACTOR

BACKGROUND OF THE INVENTION

1. Field of the Invention

The present invention relates to a reactor for conducting a continuous multi-phase catalytic reaction and is particularly, though not exclusively, applicable to the catalytic conversion of syngas, produced by the reforming of methane, to hydrocarbon fuels, by a Fischer-Tropsch type of synthesis. Other reaction systems for which the apparatus would be suitable include various slurry reactions for the production of petrochemicals, the production of oxygenates from synthesis gas and dehydrogenation reactions.

2. Description of the Invention Background

Three-phase catalytic reaction systems are used in a number of chemical processes and their application in the petrochemical industry appears to be increasing. Of the three-phase systems in use, mechanically agitated, loop and bubble column slurry reactors contain small catalyst particles dispersed in the liquid. In most applications, the liquid will have to be separated from the slurry to remove liquid products or for catalyst regeneration purposes. In those cases where the liquid is an inert medium, occasionally, it may have to be replaced due to degradation or the build-up of impurities.

Mechanically agitated slurry reactors are particularly convenient for batch processes due to the low mass-transfer and heat resistance. These features also make them suitable for the determination of reaction kinetics in the laboratory. A serious disadvantage and limitation of this reactor type, however, is the difficulty in the separation of catalyst particles in any continuous operation.

Commercially, it is only mechanically agitated reactors that are used in the hydrogenation of double bonds in oils from cottonseed, soybean, corn, sunflower, etc. By employing a nickel catalyst, the products include margarine, shortening, soap and greases. The choice of reactor is based on the low diffusivities and high viscosities of the fatty oils. Fixed-bed operation has been proposed due to the advantage of completely catalyst-free products without filtration. A number of other hydrogenation reactions are also carried out in agitated reactors, e.g. the hydrogenation of nitro compounds.

The operation of bubble column slurry reactors is simple, since mechanically moving parts are avoided. Combined with the low diffusional resistance and efficient heat transfer, these reactors are attractive for many industrial processes. However, solid-liquid separation is usually performed outside the reactor in elaborate filtering and settling systems. The catalyst slurry is to be recycled to the reactor, sometimes with the use of a slurry pump. Thus, serious problems may been countered in the continuous operation of bubble column slurry reactors.

As world oil resources diminish it is becoming more attractive to use natural gas as an energy source and methods of upgrading this to higher hydrocarbon fuels are increasing in importance.

It is therefore an object of the invention to provide a reactor which allows continuous method of conducting a multi-phase catalytic reaction which does not suffer the drawbacks of the prior art.

It is a particular object of the invention to provide such a reactor which is well suited to use in the conversion of natural gas via syngas to diesel fuel.

SUMMARY OF THE INVENTION

According to the invention, there is provided a solid/liquid slurry reaction apparatus which comprises: a reaction vessel arranged to receive the slurry; a filter member in contact with the slurry defining a filtrate zone which is separated from the slurry and having an outlet for filtrate product; means for establishing a mean pressure differential across the filter member; means for causing fluctuations or oscillations about the mean pressure differential; and means for introducing gaseous reactants or other components in the form of gas bubbles into the slurry.

Such a system is relatively simple yet effective. The separation step, generally considered to be particularly problematic, is achieved without undue complication and under proper operating conditions the filter member is self-cleaning.

Preferably, the pressure differential results from the hydrostatic pressure arising from the filter member being submerged in the slurry in the reactor. Preferably, communication between the space above the slurry in the slurry reactor and the space above the filtrate in the filtrate section prevents the build up of pressure differentials in excess of that corresponding to the hydrostatic pressure. The communication may be via a tube extending between the slurry section and the filtrate section and being open to each. The pressure fluctuations and oscillations may be caused by the turbulent motion of the slurry in the reactor. They may be transferred or enhanced, perhaps by resonance effects to the filtrate section, preferably via the tube.

Preferably, the amplitude or magnitude of the fluctuations or oscillations in the pressure differential across the filter member is about the same magnitude or greater than the mean value of the static pressure differential. Preferably the mean pressure differential across the filter member should be kept at a rather low level, typically less than 5 mBar (500 Pa). The gas contact tube may, in addition to effecting the communication between the gas phase above the slurry and the internal parts of the filter member, also provide an easy escape route for gas which may have penetrated the filter membrane and which otherwise would have become entrapped in the filtrate section.

Gaseous products or components may be allowed to escape by any convenient means such as a separate outlet from the reaction vessel or simply via the tube. Experiments carried out suggest that if the gas contact tube is closed or severely choked, the filter member would rapidly become clogged. Of course, the contact tube will set a limit to the pressure drop across the filter member and thus prevent unwanted and damaging pressure build-ups, which otherwise would probably have occurred when there is a considerable pressure drop between internal parts of the reactor and the outlet side.

The reaction apparatus may include means for applying a pulsating pressure to the filtrate zone, either directly to the filtrate, or to the gas space above the filtrate. Preferably, the pulsating pressure is provided by the action of a reciprocating piston in a cylinder. This may be in place of or in addition to the above mentioned tube.

Preferably, the filter member is in the form of a filter unit defining internally the filtrate zone and which includes a filter element separating the filtrate zone and the slurry zone. Preferably, the filter element is generally cylindrical and its axis is generally vertical in use, though it may be inclined by as much as 10 or 30 to the vertical. It may be located within the reaction vessel or in a branch member of the reaction vessel in which at least a part of the slurry phase is allowed to circulate. Preferably, the filter element comprises a fined meshed screen, helically wound threads, fine vertical threads or sintered metal particles. The filter element material and catalyst are preferably selected so that the maximum hole or pore size in the filter element is of the same order of magnitude as the catalyst particle size. The particle size preferably being not less than half the pore size. However, it would be possible for the catalyst particle size to be larger than the maximum pore size with the pore size being of the same magnitude, or less. The means for introducing gaseous reactants or components may comprise any suitable means such as a bubble cap plate, a plurality of nozzles, a frit plate, etc, preferably located at the bottom of the reaction vessel. The reactants may be CO and H for example from the reforming of natural gases, and the products may be methanol and higher hydrocarbons.

The pressure fluctuation value may be of the order of the pressure differential, for example from 10 to 200% of the pressure differential. The actual value of the pressure differential may be from 1 to 1000 mBar, preferably 2 to 50 mBar.

The pressure fluctuations may be provided by turbulent flow of the slurry in the reactor and/or by gas bubbles rising on the outside of the filter element, which may themselves give rise to turbulent flow conditions.

The vessel is preferably provided with an inlet and/or an outlet for liquid reactants or components. The filter unit member be wholly or partly filled with filtrate. Thus, the outlet from the filter unit may be connected to the tube from the filtrate section above the top of the filter unit. Alternatively, the outlet from the filtrate section may comprise a tube which is arranged to determine the level of the filtrate in the filtrate section. The filter unit may be vertically adjustable. Preferably the filtrate level is adjustable with respect to the reactor vessel.

Preferably, the reaction vessel is provided with means for heat transfer. This may comprise a plurality of vertically positioned tubes intended for circulation of a heat transfer medium.

The reactor vessel may, of course, include a plurality of filter units.

The invention is particularly well adapted for use in a method of converting natural gas (methane) to higher hydrocarbon fuels which involves initially burning reforming the methane to produce carbon monoxide and hydrogen, subjecting the CO and H to catalytic conversion by a Fischer-Tropsch synthesis to form higher hydrocarbon fuels such as liquid paraffin waxes, and subsequently separating and/or cracking these products to produce the required range of hydrocarbons.

When diesel fuel is produced in this way it is vastly superior to conventional diesel in terms of its quality and properties. Firstly, it contains no sulphur, which is important from an environmental point of view. Secondly, it has a very high cetane number and can therefore be blended with lower grades of diesel fractions in order to produce a product which meets premium range standards. Thirdly, it contains virtually no harmful compounds that generate soot when burned and needs fewer additives for problem free use at low temperatures.

BRIEF DESCRIPTION OF THE DRAWINGS

The invention may be carried into practice in various ways and some embodiments will now be described by way of example with reference to the accompanying drawings, in which.

DETAILED DESCRIPTION OF THE PREFERRED EMBODIMENTS

Figure 1:
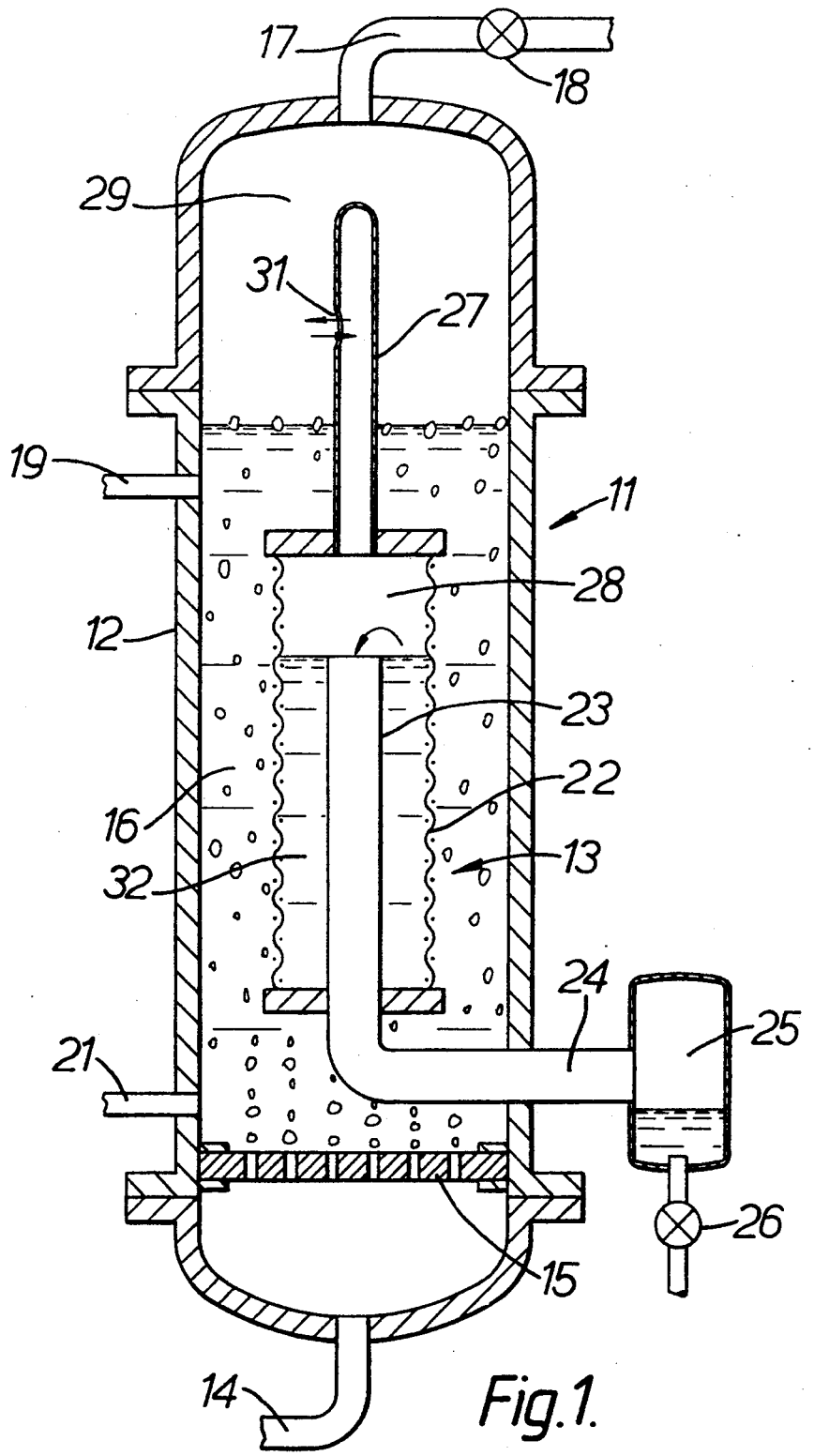
FIG. 1 is a schematic section through a three-phase slurry reactor for performing a method in accordance with the invention.

The reactor vessel 11 in FIG. 1 comprises an outer casing 12 defining the reactor vessel 11 and within the casing 12 a filter unit 13. The housing 12 has a gas inlet 14 at the bottom which, in the case of a syngas conversion process, would constitute the reactant inlet. Above the gas inlet 14, there is a gas delivery device such as a gas-permeable frit plate 15 which supports the slurry 16 in the reactor vessel 11, and at the top of the casing 12, a gas outlet 17. The gas outlet 17 is controlled by a choke or valve 18. The casing also has an inlet 19 and an outlet 21 for the slurry.

The filter unit 13 comprises a generally vertical cylindrical filter element 22 in contact with the slurry 16. The filter element is in the form of a fine meshed screen though it could alternatively comprise helically wound metal threads, sintered metal particles or narrowly separated fine vertical threads. It houses a constant level device in the form of a vertical pipe 23 which terminates below the top of the filter unit 13. The pipe 23 leads to a filtrate outlet 24 which in turn leads to a collector 25 and to an outlet valve 26. A tube 27 extends from the space 28 within the filter unit 13 above the top of the pipe 23 to the space 29 within the top of the reactor 11 above the slurry 16. An opening 31 in the tube 27 connects the two spaces 28,29.

In operation, gaseous reactants are introduced to the reactor vessel 11 via the inlet 14 and the plate 15. The reactants form bubbles in the slurry 16 which pass upwards past the filter unit 13. The slurry 16 consists of a liquid phase of the reaction products and a catalyst in finely divided form. The gaseous reactants react as they contact the catalyst, thus adding to the products in the slurry.

At the same time, the products pass through the filter element 22 to form a product filtrate 32 which is free of catalyst. Any gaseous products and unreacted reactants can be vented through the outlet 17 and subsequently treated and/or recycled. The product filtrate 32 leaves the filter unit 13 via the constant level device 23 and outlet 24 and is collected in the collector 25 for regulated continuous or periodic removal.

The difference in level between the slurry 16 and the product filtrate 32, determined by the constant level device, results in a pressure differential across the filter element 22. This helps to convey the liquid product through the filter element 22.

It might be expected that, under these conditions, the catalyst would clog the filter element, however, this is found not to be the case, provided that the pressure differential is not too great. The introduction of the reactants together with the connection of the gas spaces 28, 29, and the generally turbulent conditions in the reactor vessel 11 combine to cause fluctuations in the pressure differential across the filter element 22. These in turn cause fluctuations in the liquid flow through the filter element 22 resulting in an anti-clogging effect. This may be enhanced by the movement of the gas bubbles past the surface of the filter element 22.

Figure 2:
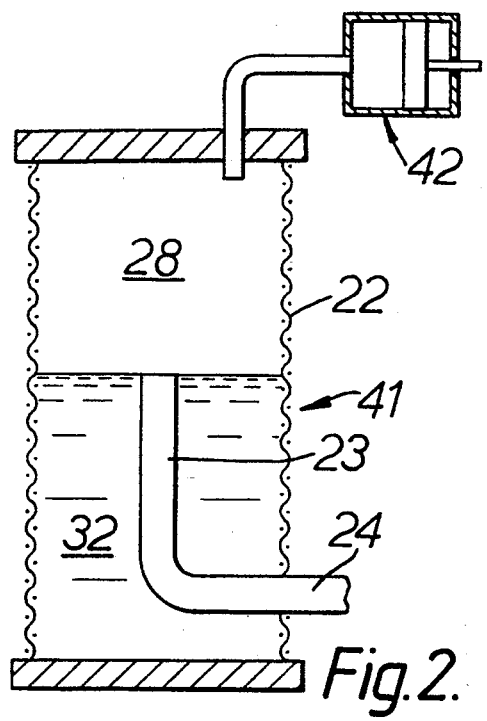
FIG. 2 is a simplified schematic section through a part of a reactor showing an alternative system for achieving the fluctuations in pressure.

An alternative embodiment is shown in FIG. 2. In this case the filter unit 41 has no tube 27 connecting the space 28 to the space 29 in the reactor (not shown). Instead, a cylinder and piston assembly 42 is connected to the space 28. By reciprocating the piston, a pulsating pressure is produced resulting in the desired fluctuation in the pressure differential across the filter element 22. This arrangement can of course be used in conjunction with the embodiment shown in FIG. 1. Communication between the spaces above the slurry and the filtrate may be provided by a tube (not shown) having a restriction or choke limiting the transmission of pressure pulses to the space above the slurry, which would otherwise have tended to eliminate the net effect of the reciprocating piston. The tube would nevertheless control the static pressure differential.

The constant level device 23 can be made adjustable in order to provide a degree of control over the pressure differential across the filter element 22. Three ways in which this can be achieved are shown in FIGS. 3, 4 and 5.

Figure 3:
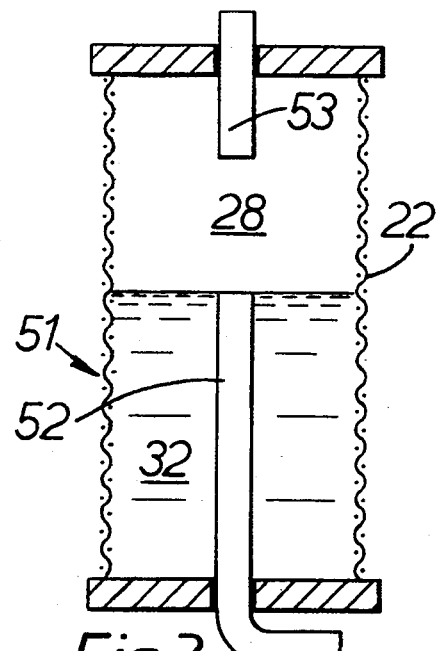
FIGS. 3, 4 and 5 are views similar to FIG. 2 showing three ways of adjusting the pressure differential across the filter member.

In the filter unit 51 of FIG. 3, both the vertical pipe 52 and the tube 53 are slidably mounted with respect to the filter unit 51. In the filter unit 61 of FIG. 4, the vertical pipe 62 is slidably mounted but the tube 63 is fixed relative to the filter unit 61. In the filter unit of FIG. 5, the tube 73 is fixed, and the vertical pipe 72 is slidably mounted within a fixed sleeve 74. Thus, the level of the filtrate 32 remains fixed relative to the filter unit 71 as it is raised or lowered.

Figure 4:
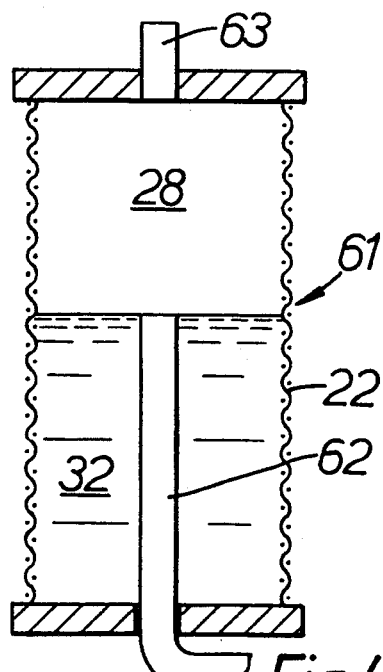
Figure 5:
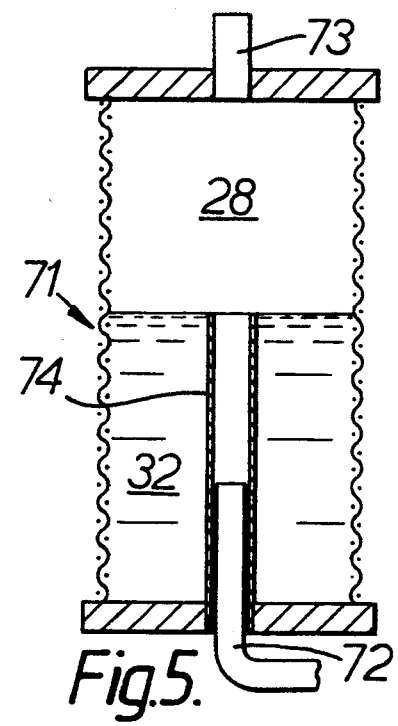

The variants shown in FIGS. 3 to 5 can be combined with either of the embodiments shown in FIGS. 1 and 2.

Figure 6:
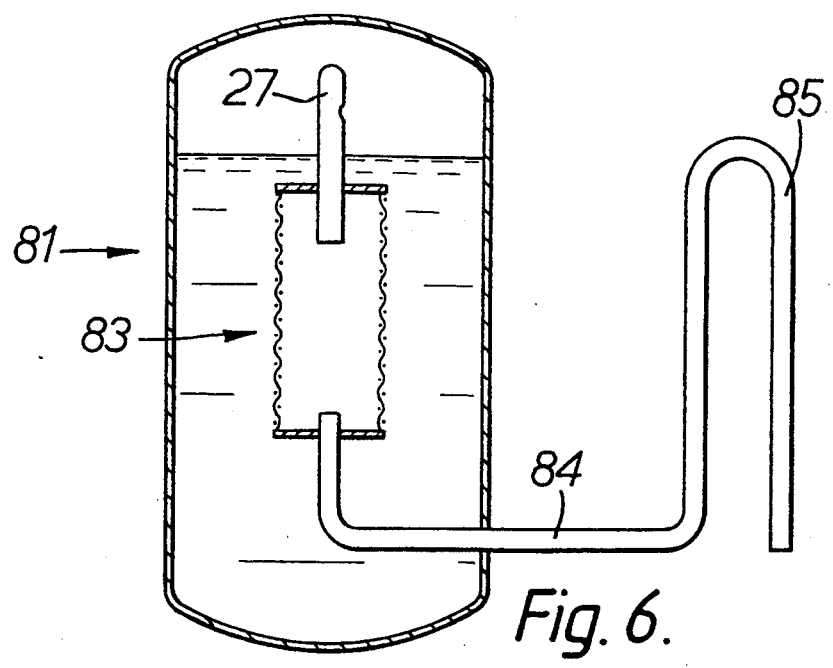
FIGS. 6 and 7 are two further alternative embodiments.
Figure 7:
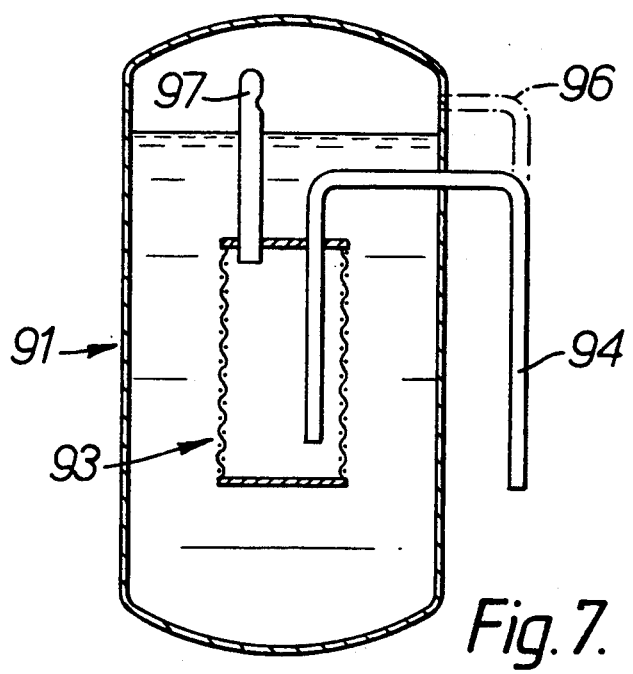

In the reactor 81 shown in FIG. 6, the outlet 84 from the filter unit 83 has an upward loop 85 to ensure that the filter unit 83 is filled with liquid. In the reactor 91 shown in FIG. 7, there is a tube 97 connecting the gas space in the reactor to the filtrate. The outlet 94 extends to the bottom of the filter unit 93 and there is an optional connection 96 between the outlet 94 and the space in the reactor. This connection 96 would tend to prevent any siphon effect and allow any gas remaining in the filtrate to escape. Again, the filter unit 93 will be filled with filtrate.

In all the illustrate embodiments, the geometries of the reactor, the communication means (eg. the tube 27) and the filtrate section may be varied in size and in order to optimise the pressure fluctuations by exploiting resonance-like effects.

The invention will now be further illustrated in the following Examples which were conducted on a laboratory scale.

EXAMPLE I

A stainless steel tube, with a diameter of 4.8 cm and a height of approximately 2 meters was filled with a hydrocarbon liquid and a fine powdered catalyst. The tube was operated as a slurry bubble column by bubbling gas through the slurry.

A filter unit was placed in the upper part of the reactor. The filter unit was made of Sika stainless steel sintered metal cylinder Type R20 produced by the company Pressmetall Krebsöge Gmbh. The filter unit had an outer diameter of 2.5 cm, a height of 25 cm, and an average pore size of 20 μm.

In this particular experiment, the reactor was filled with a slurry consisting of a poly α-olefin liquid and approximately 10 weight % of a fine powdered cobalt on alumina catalyst. The particle size ranged from 30 to 150 μm. The catalyst was kept suspended by gas bubbling through the liquid. The gas was a mixture of $H_2CO$ and $N_2$ of varying composition, and was fed with a superficial gas velocity of 4 cm/s. The temperature in the reactor was 230° C. and the pressure was 30 bar ($3 \times 10^6$ Pa).

The filtrate level inside the slurry was set approximately half way up in the valve.

The liquid formed by the Fischer-Tropsch reaction in the reactor was withdrawn through the filter unit. In addition, a poly α-olefin liquid fed to the reactor was also withdrawn through the filter unit. The liquid withdrawal varied from 320 to 2.5 g/h depending on the formation rate of the liquid product, and the feeding rate of the hydrocarbon liquid. The experiment lasted approximately 400 hours, and a total amount of liquid of 30 liters was withdrawn through the filter unit. The liquid level in the reactor was constant during the experiment, and no colour indicating presence of solid particles could be observed in the liquid.

EXAMPLE II

A glass tube, with a diameter of 22 cm and a height of 2.5 meters was filled with hydrocarbon liquid (Monsanto heat transfer fluid, MCS 2313) and a fine alumina powder (average particle diameter approximately 75 μm). The content of alumina was approximately 15% by weight. The tube was operated as a slurry bubble column (SBC) by bubbling gas through the slurry.

A filter member without a connection tube between the gas volume above the slurry phase and the gas volume above the product phase was placed in the upper part of the SBC. The filter member was made of a sika fil 10 stainless steel sintered metal cylinder produced by Sintermetallwerk Krebsöge GmbH. The sinter cylinder had an outer diameter of 2.5 cm, a height of 20 cm, and an average pore size of 10 μm.

In this particular experiment the slurry level was set to be at the top of the sinter cylinder. The pressure amplitude in the SBC was measured to be 6 mBar, the pressure drop across the sinter metal wall was approximately 3–4 mBar (300–400 Pa). The temperature in the slurry was 200° C., the pressure was 1 Bar ($10^5$ Pa) and the gas velocity was approximately 6 cm/s.

At the start of the experiment, the flow of the filtrate through the sinter metal cylinder was about 1000 ml per minute. After 4 hours the flow was reduced to zero due to clogging of the sinter metal wall on the slurry side.

When a similar experiment was carried out in an apparatus in which communication between the gas volumes was provided by a piece of pipe acting as a connection tube, the initial flow rate was maintained essentially at the same level throughout the experiment. It was therefore concluded that the absence of a connection tube between the gas volume above the slurry and the gas volume above the product phase resulted in clogging in the first experiment.

We claim:

1. Apparatus for conducting a continuous multi-phase catalytic reaction in a slurry bubble column comprising:
    (a) a reaction vessel defining a reaction zone therein, said reaction zone being arranged to receive a slurry;
    (b) a filter member in contact with said reaction zone defining a filtrate zone separated from said reaction zone and having an outlet;
    (c) means for maintaining a predetermined mean pressure differential across said filter member; and
    (d) a gas distribution device in said reaction zone, adapted to introduce gaseous components in the form of a stream of bubbles into said slurry in said reaction zone, said stream of bubbles serving to maintain said slurry in a state of constant agitation and to cause fluctuations about said mean pressure differential.

2. Apparatus according to claim 1, wherein said reaction zone and said filtrate zones include a gas space thereabove and interconnecting means is provided interconnecting said gas spaces with said filtrate zone.

3. Apparatus according to claim 2, wherein said interconnecting means comprises a tube extending between said reaction zone and said filtrate zone and being open to each.

4. Apparatus according to claim 1, wherein said predetermined mean pressure differential is 5 mBar (5 Pascals).

5. Apparatus according to claim 4, wherein the amplitude of said fluctuations about said mean pressure differential are from about 10 percent to about 200 percent of the magnitude of said mean pressure differential.

6. Apparatus according to claim 5, wherein the amplitude of said fluctuations about said mean pressure differential is about the same magnitude as the magnitude of said mean pressure differential.

7. Apparatus according to claim 1, further comprising a means for providing additional pressure pulsations to said filtrate zone.

8. Apparatus according to claim 7, wherein said means for providing additional pressure pulsations comprises a movable piston in a cylinder connected to said filtrate zone above a liquid level therein.

9. Apparatus according to claim 1, further comprising an outlet for gaseous components from said reaction vessel.

10. Apparatus according to claim 1, wherein said filter member is generally cylindrical and in use generally vertical.

11. Apparatus according to claim 1, wherein said filter member is located within said reaction vessel.

12. Apparatus according to claim 1, further comprising a branch member and wherein said filter member is arranged in said branch member and wherein at least a part of said slurry is arranged to circulate through said branch member.

13. Apparatus according to claim 1, further comprising a means for maintaining a predetermined liquid level in said filtrate zone.

14. Apparatus according to claim 13, wherein said means for maintaining said predetermined liquid level in said filtrate zone is adjustable to vary said liquid level.

15. Apparatus according to claim 13, wherein said means for maintaining said predetermined liquid level in said filtrate zone comprises an outlet tube having an opening located in said filtrate zone, wherein said liquid level is maintained at the level of said outlet tube opening, said outlet tube constituting the outlet from said filtrate zone.

16. Apparatus according to claim 15, further comprises means for vertically moving said tube opening to vary the liquid level in said filtrate zone.

17. Apparatus according to claim 1, further comprising means for vertically moving said filter member.

18. Apparatus according to claim 1, wherein said filter member is in the form of a filter unit defining said filtrate zone, said filter member including a filter element separating said filtrate zone and said reaction zone.

19. Apparatus according to claim 18, wherein said filter element comprises sintered metal particles.

20. Apparatus according to claim 18, wherein said filter element comprises a fine meshed screen.

21. Apparatus according to claim 18, wherein said filter element comprises helically wound threads.

22. Apparatus according to claim 1, wherein said means for introducing gaseous components comprises a frit plate at the bottom of said reaction vessel.

23. Apparatus according to claim 1, wherein said reaction vessel is provided with a further inlet and a further outlet for liquid components.

24. Apparatus according to claim 1, wherein said reaction vessel is provided with means for heat transfer.

25. Apparatus according to claim 20, wherein said means for heat transfer comprises a plurality of tubes containing a heat transfer medium.

26. Apparatus according to claim 1, including a plurality of said filter members within said reaction vessel.

27. Apparatus for conducting a continuous multi-phase catalytic reaction comprising:
    (a) a vertical reaction vessel having a reaction zone for containing a slurry, a gas entry zone located below said reaction zone and separated therefrom by a fritted disk whereby gas in said gas entry zone flows through said fritted disk and forms bubbles which flow upward through said slurry when said slurry is in said zone;
    (b) a filter enclosure defining therein a filtrate zone and being positioned within said reaction zone, said filter enclosure being structured to permit liquid to flow through said filter enclosure into said filtrate zone;
    (c) a tube interconnecting said filtrate zone with said reaction zone above the level of said slurry; and
    (d) a liquid outlet from said filtrate zone, said outlet comprising a pipe having an opening within said filtrate zone, whereby a liquid level in said filtrate zone is maintained at the level of said opening.

* * * * *

UNITED STATES PATENT AND TRADEMARK OFFICE
CERTIFICATE OF CORRECTION

PATENT NO. : 5,407,644
DATED : Apr. 18, 1995
INVENTOR(S) : Erling Rytter, et al

It is certified that error appears in the above-indentified patent and that said Letters Patent is hereby corrected as shown below:

On title page, item [22],

Delete "Filed: Feb. 24, 1995" and substitute therefor --Filed: Feb. 24, 1993--.

Signed and Sealed this

Twenty-third Day of April, 1996

Attest:

BRUCE LEHMAN

Attesting Officer

Commissioner of Patents and Trademarks